(12) United States Patent
Consolante

(10) Patent No.: US 10,401,148 B2
(45) Date of Patent: Sep. 3, 2019

(54) APPARATUS AND METHOD FOR ACQUIRING DATA RELATIVE TO A DIMENSION OF AN ELONGATED OBJECT

(71) Applicant: PHILIP MORRIS PRODUCTS S.A., Neuchatel (CH)

(72) Inventor: Antonio Consolante, Casalecchio di Reno (IT)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 16/063,890

(22) PCT Filed: Dec. 20, 2016

(86) PCT No.: PCT/EP2016/081967
§ 371 (c)(1),
(2) Date: Jun. 19, 2018

(87) PCT Pub. No.: WO2017/108819
PCT Pub. Date: Jun. 29, 2017

(65) Prior Publication Data
US 2018/0372482 A1    Dec. 27, 2018

(30) Foreign Application Priority Data

Dec. 21, 2015 (EP) .................................. 15201699

(51) Int. Cl.
*G01B 11/14* (2006.01)
*G01B 11/04* (2006.01)
(Continued)

(52) U.S. Cl.
CPC ............ *G01B 11/04* (2013.01); *A24C 5/3412* (2013.01); *G01B 11/10* (2013.01); *G02B 5/04* (2013.01); *G01N 21/952* (2013.01)

(58) Field of Classification Search
CPC ......... G01B 11/24; G01B 11/02; G01B 11/14; G03F 7/70625; G01N 21/4788
(Continued)

(56) References Cited

U.S. PATENT DOCUMENTS

2006/0098214 A1    5/2006    Wilson

FOREIGN PATENT DOCUMENTS

EP          2568279         3/2013
WO    WO 2012/053365       4/2012

OTHER PUBLICATIONS

PCT Search Report and Written Opinion for PCT/EP2016/081967 dated Mar. 14, 2017 (11 pages).

*Primary Examiner* — Md M Rahman
(74) *Attorney, Agent, or Firm* — Mueting, Raasch & Gebhardt, P.A.

(57) ABSTRACT

The present invention relates to an apparatus for acquiring data relative to a dimension of an elongated object defining a longitudinal axis and a first and a second end, the apparatus comprising: an imaging sensor device defining a field of view and an optical axis, the imaging sensor device being adapted to image the elongated object in the field of view; a transporting device adapted to position the elongated object in the field of view and to transport the elongated object in a transport direction substantially parallel to the longitudinal axis of the elongated object and forming an angle with the optical axis; an illuminating device adapted to emit electromagnetic radiation to illuminate the elongated object in the field of view; and an optical deflection system including an optical deflector which is adapted to be movable between a first operative position where it is located outside the field of view of the imaging sensor device and a second operative position where it is located within the field of view of the imaging sensor device, and which is adapted to deflect electromagnetic radiation travelling parallel to the (Continued)

longitudinal axis towards said imaging sensor device so as to obtain an image of the first or of the second end of the elongated object. The present invention also relates to a method for acquiring data relative to a dimension of an elongated object defining a longitudinal axis and having a first and a second end.

18 Claims, 1 Drawing Sheet

(51) Int. Cl.
*A24C 5/34* (2006.01)
*G01B 11/10* (2006.01)
*G02B 5/04* (2006.01)
*G01N 21/952* (2006.01)

(58) Field of Classification Search
USPC .......................................................... 356/625
See application file for complete search history.

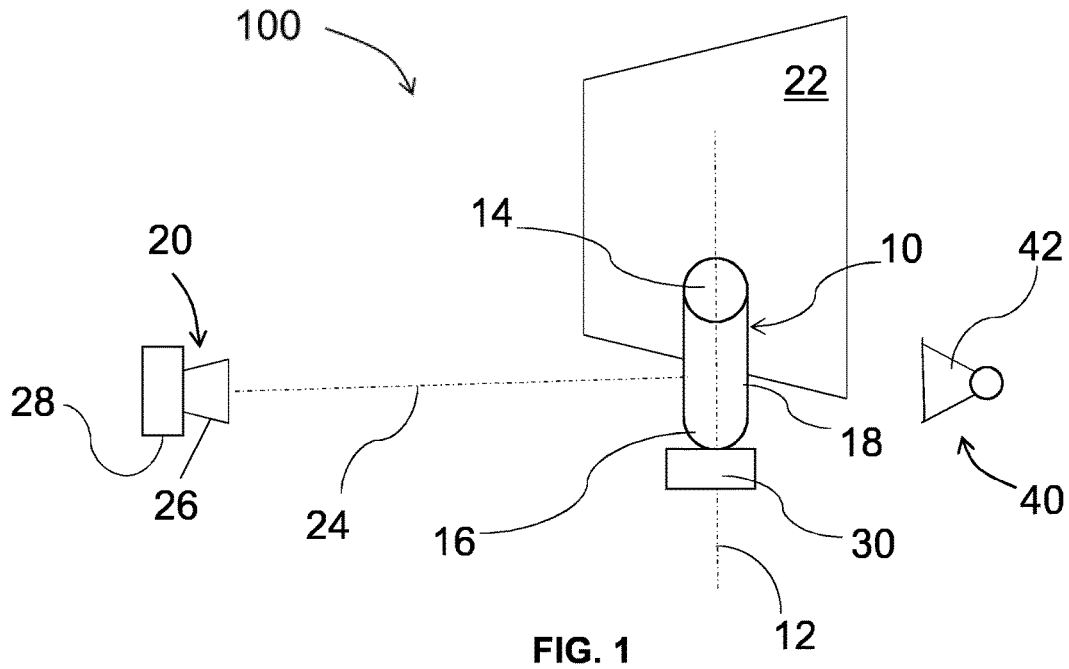
FIG. 1
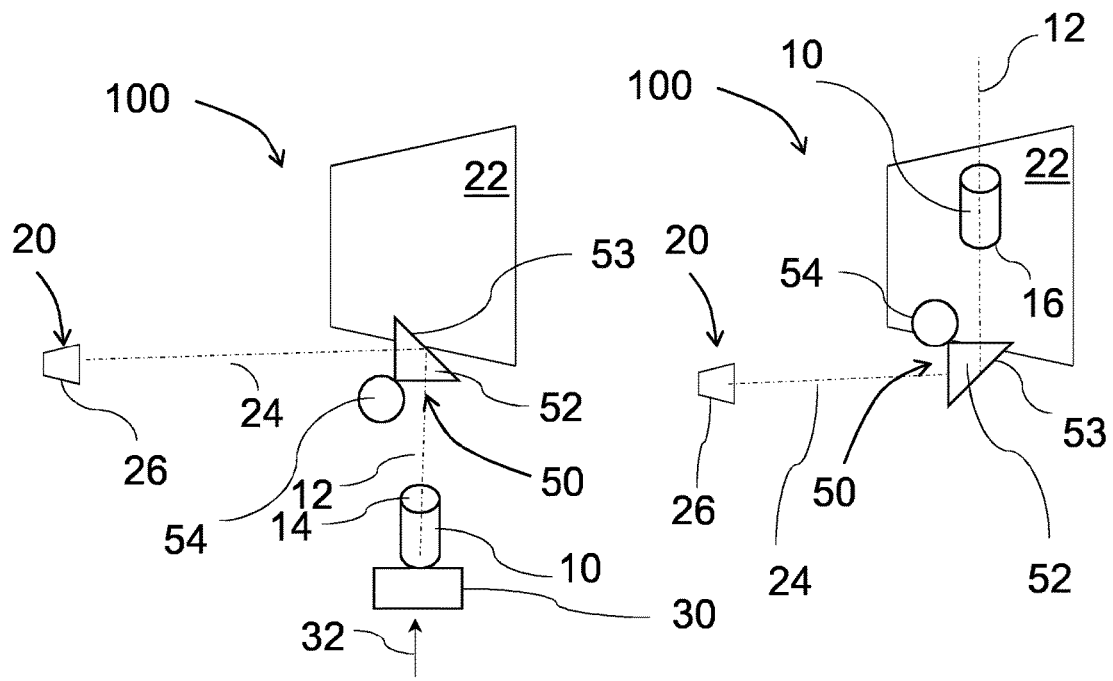
FIG. 2 FIG. 3

APPARATUS AND METHOD FOR ACQUIRING DATA RELATIVE TO A DIMENSION OF AN ELONGATED OBJECT

This application is a U.S. National Stage Application of International Application No. PCT/EP2016/081967, filed Dec. 20, 2016, which was published in English on Jun. 29, 2017, as International Publication No. WO 2017/108819 A1. International Application No. PCT/EP2016/081967 claims priority to European Application No. 15201699.4 dated Dec. 21, 2015.

The present invention relates to an apparatus and a method for acquiring data relative to a dimension of an elongated object, preferably of a component of an aerosol-forming article.

It is known that aerosol-forming articles, such as smoking articles, can be realized by the combination of several components, such as filter plugs or consumable rods (such as tobacco rods). Each of the components used in aerosol-forming articles should respect numerous and very strict constraints, for instance regarding their dimensions. For this purpose, during manufacturing process, tests are performed on same sample components to check whether they satisfy the aforementioned requirements.

It is also known that the production of components for aerosol-forming articles is realized at a very high speed. In order to minimize the wasted material, once a component sample has been targeted for tests, the tests are preferably realized also at very high speed so that a possible faulty production batch could be identified as quickly as possible in order for example to find out the cause of the problem which caused the fault.

The number of measurements necessary to verify that a component satisfy the desired requirements is relatively high, because substantially all dimensions and geometrical characteristics of the component, such as its cross section, its homogeneity in shape, etc., are to be checked. However, on the one hand, having a wide plurality of sensors to measure simultaneously several data of the component is not a solution because the sensors could be hindering or disturbing each other and furthermore there should be enough room for the components to be moved in the test area without damage or interruption of production. On the other hand, moving a sensor at high speed around the component to measure several component's dimensions is also not satisfactory because the sensor mechanism could be damaged or lose calibration because of such high speed movements.

There is therefore a need for a method and apparatus of acquiring data relative to an elongated object, preferably a component of an aerosol-forming article, in which several measurements of the object can be obtained at high speed. Further, there is a need for a method and an apparatus in which this plurality of measurement is realized in a rather simple manner without the use of relatively expensive devices.

In a first aspect thereof, the invention relates to an apparatus for acquiring data relative to a dimension of an elongated object defining a longitudinal axis and a first and a second end, the apparatus comprising: an imaging sensor device defining a field of view and an optical axis, the imaging sensor device being adapted to image the elongated object in the field of view; a transporting device adapted to position the elongated object in the field of view and to transport the elongated object in a transport direction substantially parallel to the longitudinal axis of the elongated object and forming an angle with the optical axis; an illuminating device adapted to emit electromagnetic radiation to illuminate the elongated object in the field of view; and an optical deflection system including an optical deflector which is adapted to be movable between a first operative position and a second operative position and which is adapted, in the second operative position, to deflect electromagnetic radiation travelling parallel to the longitudinal axis towards said imaging sensor device so as to obtain an image of the first or of the second end of the elongated object.

Advantageously, the apparatus of the invention is neither complex, nor expensive and allows high speed testing of the elongated objects. In particular, the apparatus of the invention may achieve quick imaging of side and ends of the elongated object. The apparatus of the invention may comprise a single imaging sensor device, which can image both end(s) and side of the elongated objects, so that there is no risk of disturbances between a plurality of sensors, each for a different elongated object's view. Furthermore, there is preferably enough room for the elongated objects to be moved in the test area without damage or interruption of production. Moreover, it is preferably not necessary to move the imaging sensor device at high speed around the elongated object in order to obtain all the desired images, so that there is a very limited risk of damage or lose calibration of the imaging sensor device.

Preferably, the elongated object includes a component of an aerosol-forming device. Preferably, the elongated object may include more than one component of an aerosol-forming article. Preferably, the elongated object may include the whole aerosol-forming article. In the following, with the term "component" any element which may be included in an aerosol-forming article is meant. For example, such component might include a plug of a filter, a heat source, a menthol capsule, a charcoal element, and so on.

Preferably, the component of the aerosol-forming article comprises a tobacco-containing material including volatile tobacco flavour compounds, which are released from the substrate upon heating. The aerosol-forming substrate may comprise, for example, one or more of: powder, granules, pellets, shreds, spaghettis, strips or sheets containing one or more of: herb leaf, fragments of tobacco ribs, reconstituted tobacco, homogenised tobacco, extruded tobacco and expanded tobacco.

Preferably, the component of the multicomponent aerosol-forming article comprises a segment of a filter of an aerosol-forming article. The filter may comprise a cellulose acetate filter plug. The filter may have a length of between about 5 millimeters and about 20 millimeters, for example of about 7 millimeters in length.

Preferably, the component of the aerosol-forming article is a tobacco containing component. The tobacco component might contain a tobacco cut filler or an aerosol-forming reconstituted tobacco. The component may comprise a tobacco rod to be combusted.

Preferably, the component of the aerosol-forming article may include a heat source, or a volatile flavour generating component, for example a menthol capsule, a charcoal element, etc. The heat source may comprise a combustible high carbon content carbonaceous material and also can include graphite or alumina. The heat source is for example a charcoal element that may be ignited and transfer heat to the aerosol-forming substrate to form an inhalable aerosol.

The volatile flavour generating component may be coupled to a fibrous support element. The fibrous support element may be any suitable substrate or support for locating, holding, or retaining the flavour generating component. The fibrous support element may be, for example, a paper support or a capsule. The fibrous support may be, for example, a thread or twine. Such thread or twine may be saturated in a liquid component, such as liquid menthol. Such a thread or twine may be threaded to or otherwise coupled to a solid flavour generating component. For example, solid particles of menthol may be coupled to a thread.

The elongated object defines a longitudinal axis. Any lateral view of the elongated object taken parallel to the longitudinal axis therefore defines a view of a "side" of the elongated object. Any view of the elongated object taken perpendicularly to the longitudinal axis defines an "end" view of the elongated object. Commonly, but not always, two lateral views of two sides of the elongated object taken by rotating the elongated object by 360° around an axis perpendicular to the longitudinal axis from one view to the other, and two top and bottom view of the two ends of the elongated object, also taken by rotating the elongated object by 180° around an axis perpendicular to the longitudinal axis, represent a full imaging of all surfaces of the elongated object.

Preferably, the elongated object might be rod shaped.

In the following, the term "length", unless otherwise specified, refers to a length of the elongated object along its longitudinal axis.

In the following, the term "rod" denotes a generally cylindrical element of substantially cylindrical, oval or elliptical cross-section.

Aerosol-forming articles according to the invention may be whole, assembled aerosol-forming articles or components of aerosol-forming articles that are combined with one or more other components in order to provide an assembled article for producing an aerosol, such as for example, the consumable part of a heated smoking device.

As used herein, aerosol-forming article is any article that generates an inhalable aerosol when an aerosol-forming substrate is heated. The term includes articles that comprise an aerosol-forming substrate that is heated by an external heat source, such as an electric heating element. An aerosol-forming article may be a non-combustible aerosol-forming article, which is an article that releases volatile compounds without the combustion of the aerosol-forming substrate. An aerosol-forming article may be a heated aerosol-forming article, which is an aerosol-forming article comprising an aerosol-forming substrate that is intended to be heated rather than combusted in order to release volatile compounds that can form an aerosol. The term includes articles that comprise an aerosol-forming substrate and an integral heat source, for example a combustible heat source.

Aerosol-forming articles according to the present invention may be in the form of filter combustible cigarettes or other smoking articles in which tobacco material is combusted to form smoke.

An aerosol-forming article may be an article that generates an aerosol that is directly inhalable into a user's lungs through the user's mouth. An aerosol-forming article may resemble a conventional smoking article, such as a cigarette and may comprise tobacco. An aerosol-forming article may be disposable. An aerosol-forming article may be partially-reusable and comprise a replenisheable or replaceable aerosol forming substrate.

Preferably, the aerosol-forming article may be substantially cylindrical in shape. The aerosol-forming article may be substantially elongated. The aerosol-forming article may have a length and a circular cross-section substantially perpendicular to the length. The aerosol-forming article may have a total length between about 30 millimeters and about 100 millimeters. The circular cross-section of the aerosol-forming article may have a diameter between about 5 millimeters and about 12 millimeters.

The apparatus of the invention comprises an imaging sensor device adapted to detect and convey the information that constitutes an image. The imaging sensor device may be either analog or digital. The digital sensor device may be a digital camera, a camera module, an imaging equipment, a night vision equipment such as thermal imaging devices, radar, sonar, and others.

Imaging sensor device preferably includes an image sensor. Analog sensors for visible light may include a video camera tube, digital sensors may include semiconductor charge-coupled devices (CCD), or active pixel sensors in complementary metal-oxide-semiconductor (CMOS) or N-type metal-oxide-semiconductor (NMOS, Live MOS) technologies. Analog sensors for invisible radiation may include vacuum tube.

The imaging sensor device preferably also comprises an optical system which defines an optical axis and a field of view. The optical axis is, in an approximation of light propagation as "straight lines", an imaginary line that defines the path along which light propagates through the optical system and reaches the image sensor in order to form an image. The field of view is a solid angle through which the image sensor is sensitive to electromagnetic radiation. Therefore, lights coming from or reflected by objects which are positioned within the field of view may be received by the image sensor device so that an image of the object is formed.

The apparatus further comprises a transporting device adapted to position the elongated object in the field of view of the imaging sensor device and to transport the elongated object in a transport direction substantially parallel to the longitudinal axis of the elongated object. The transporting device can be of any type, for example it may include a conveyor belt. The transporting device brings the elongated object positioned with its longitudinal axis parallel to the transport direction within the field of view of the imaging sensor device so that at least a side of the elongated object, the one towards the imaging sensor device, can be imaged. The transporting device in its movement along the transport direction allows taking images of a side of the elongated object at various positions, approaching and moving away from the image sensor. The transport direction forms an angle with the optical axis, this angle is different from 0° and 180°, that is, the transport direction is not parallel to the optical axis otherwise no image can be taken of the elongated object.

Further, the apparatus includes an illuminating device. The illuminating device emits an electromagnetic radiation, for example visible light but any other radiation is encompassed by the present invention in order to illuminate the elongated object. For example, the illuminating device may include a light emitting diode (LED) or a laser source. The type of radiation emitted by the illuminating device depends on the type of image sensor chosen, that is, which wavelength range the image sensor is sensitive to. The illuminating device could be positioned with respect to the image sensor as a front light, that is, it illuminates the elongated object from behind or at the image sensor location when the elongated object is positioned within the field of view of the image. The front light is radiation directed towards the object and away from the image sensor. The illuminating device could be positioned with respect to the image sensor as a back light, that is, the illumination device is located behind the elongated object shining towards the image sensor, when the elongated object is positioned within the field of view of the image. The back light is radiation directed towards the object and towards the image sensor.

With the above configuration, it is clear that an image of at least a side of the elongated object can be obtained. The transporting device transports the elongated object along the transport direction which is parallel to the longitudinal axis of the elongated object. When the elongated object reaches the field of view of the imaging sensor device, one side of the elongated object is facing the imaging sensor device, it is illuminated by the illuminating device and therefore an image of the side can be taken. Preferably more than one image can be taken, at different distances between the imaging sensor device and the elongated object along the longitudinal direction. The imaging sensor device preferably takes an image of a side of the elongated object directly, without the use of any additional mirror or optical elements to divert the light path of electromagnetic radiation illuminating the elongated object. The elongated object is in the field of view of the imaging sensor device and an image of the side of the same is preferably taken directly.

The apparatus also comprises an optical deflection system including an optical deflector. The optical deflector is movable between a first operative position where it is substantially not used and a second operative position where it is located in a position where it can send electromagnetic radiation towards the imaging sensor device. In the first operative position, the optical deflector does not contribute to any further image of the elongated object because it is positioned in such a way that cannot send radiations towards the field of view of the imaging sensor device. Further, in the first operative position, the optical deflector does not hinder the movement or transport of the elongated object by means of the transporting device. On the contrary, in the second operative position, it can sent radiation towards the field of view of the imaging sensor device because it is placed in such a location that it is able to deflect electromagnetic radiation travelling parallel to the longitudinal axis of the elongated object towards said imaging sensor device. The electromagnetic radiation travelling parallel to the longitudinal axis of the elongated object carries information relative to one end of the elongated object itself, therefore the imaging sensor device can obtain an image of one of the end of the elongated object. An "end" of the elongated object can preferably be imaged by the imaging sensor device "indirectly", that is, with the use of the optical deflector which deflect electromagnetic radiations and directs it towards the imaging sensor device.

Using a relatively simple construction, the apparatus of the invention may obtain images of both a side and one of the ends of the elongated object. The imaging sensor device does not need to move in order to obtain these images of different areas of the elongated object, in particular it does not need to move at high speed, but a simpler optical deflector makes a substantially simple movement from a first to a second operative position, for example by means of a translation of the optical deflector. Therefore, two different images can be obtained in a rather easy manner.

The transporting device allows moving the elongated object that is tested along the longitudinal axis of the elongated object itself, as well as rotating the elongated object according to the longitudinal axis.

Preferably, said optical detector includes a prism adapted to be positioned in front of an end of the elongated object and having a facet angled with respect to the transport direction. More preferably, an angle formed between the transport direction and the facet of the prism is comprised between about 30° and about 60° and even more preferably the angle is of about 45°.

Advantageously, the prism is an optical prism with a triangular section and rectangular sides. Such optical prism is preferably made of glass. The prism is a rather "robust" and simple component and movements of the same are possible without damaging the prism itself. The selected angle of the facet of the prism and the optical axis, for example preferably between 30° and 60°, allows an easy redirecting of light towards the imaging sensor device. Preferably, the prism has a triangular cross section that has the shape of an isosceles triangle. Preferably, the isosceles triangle has a 90° angle and two 45° angles, so that such triangular cross section is a right isosceles triangle, having a base and two legs. Due to the fact that the critical angle of glass in air is 42°, incoming light going inside the prism perpendicularly to one of the rectangular sides of the prism, corresponding to one of the legs of the triangular cross section, is reflected at 90°. Such prism, being made of a strong material without electronic or mechanism inside, can be advantageously moved at high speed.

Preferably, the transport direction is substantially perpendicular to the optical axis. An image of the elongated object in this case may not need to be elaborated due to the inclination between optical axis and transport direction in order to obtain the correct dimension of the elongated object. A perpendicularity between optical axis and transport direction therefore may simplify the image elaboration for obtaining one or more dimensions or characteristics of the elongated object.

More preferably, the imaging sensor device includes a fixed focus camera and said transporting device is adapted to transport said elongated object along the transport direction lying in a fixed focus plane of said imaging sensor device. Advantageously, the imaging sensor device has a fixed focus. Preferably, therefore, the transport direction lies on the focus plane of the imaging sensor device, so that the elongated object, when within the field of view, is always at focus and several images with varying position along the transport direction may be taken.

Preferably, the transporting device is adapted to rotate the elongated object around the longitudinal axis. Two or more sides of the elongated object may be captured by means of images by the apparatus of the invention.

Preferably, in said second operative position, the optical deflector is located at a geometrical intersection between the transport direction and the optical axis. This configuration may simplify the geometry of the system and reduces the elaboration of the images to obtain the correct real dimensions of the elongated object.

Preferably, the optical deflection system includes an optical deflector holder adapted to rotate the optical deflector so that the second operative position comprises a first sub-position in which electromagnetic radiation travelling parallel to the longitudinal axis in a first versus is deflected towards said imaging sensor device so as to obtain an image of the first end of the elongated object and a second sub-position in which electromagnetic radiation travelling parallel to the longitudinal axis in a second versus is deflected towards said imaging sensor device so as to obtain an image of the second end of the elongated object. Advantageously, the apparatus of the invention allows to take an image of the elongated object from a side direction, from an end direction, and from an opposite end direction, without rotating the elongated object. When rotation is added, more than one side of the elongated object can be detected.

Therefore, with the apparatus of the invention substantially the whole external surface of the elongated object can be imaged.

Preferably, the image sensor device includes an image sensor holder and an image sensor, the image sensor holder being adapted to translate the image sensor along the optical axis. Advantageously, the image sensor is moved only along the optical axis, so that the image sensor is focused on what is to be captured. Therefore, different elongated objects may be used, and the imaging sensor device is moved to focus on the elongated object positioned in the transporting device.

Preferably, the illuminating device comprises one or more of the following: a back light positioned along the optical axis on an opposite side of the transport direction with respect to the imaging sensor device, the back light being adapted to irradiate a surface of the elongated object facing the back light; a front light positioned along the optical axis on a same side of the transport direction with respect to the imaging sensor device, the front light being adapted to irradiate a surface of the elongated object facing the imaging sensor device. Advantageously, the illuminating device may allow creating a back light from behind the elongated object toward the imaging sensor device. The back light may be strong enough comparing to the sensitivity of the imaging sensor device, so that in case an elongated object is in the path of light toward the imaging sensor device, the back light goes through any void between the elongated object components up to the imaging sensor device. In this way, the back light allows estimating the positions of the components of the elongated object. Advantageously, the illuminating device may allow creating a front light from the imaging sensor device toward the elongated object, so as to illuminate a surface of the elongated object. Images obtained using the front light may be used to calculate a length of the elongated object or to check a wrapping paper position on the elongated object.

Preferably, the apparatus according to the invention comprises an elaborating unit, adapted to compute a value of a dimension of the elongated object from the image acquired by the imaging sensor device. Different positions of the elongated object (after moving it along its longitudinal axis and rotating it) may be captured by the imaging sensor device. The data captured by the imaging sensor device are sent to the elaborating unit to be processed. Advantageously the data are used, for instance, to calculate ovalization, diameter or length of the elongated object or, for instance, to check a wrapping paper position on the elongated object.

Usually, elongated objects are cylindrical, but any other shape of the elongated objects can be tested by the invention.

Preferably, the elongated object is put by the transporting device at a specific position in field of view.

The image sensor of the imaging sensor device is, for instance, a camera which preferably has no auto-focus, but a fixed focus distance. An algorithm or software, running on the elaborating unit, indicates if the image taken by the camera is focused or not, sends command to the image sensor holder of the imaging sensor device to move the camera accordingly.

By doing so, the distance from the camera to the elongated objects becomes equal to the fixed and known focus distance, and all the images taken by the camera, whatever the elongated objects, are in the same scale and focus and can be compared to each other and to reference.

In a second aspect thereof, the invention relates to a method for acquiring data relative to a dimension of an elongated object defining a longitudinal axis and having a first and a second end, the method comprising the step of: providing an imaging sensor device having an optical axis and a field of view; moving the elongated object along a transport direction parallel to the longitudinal axis and forming an angle with the optical axis in the field of view of the imaging sensor device; irradiating the elongated object by means of electromagnetic radiation; and deflecting electromagnetic radiation travelling parallel to the longitudinal axis towards said imaging sensor device so as to form an image of one of the ends of the elongated object.

The advantages of the second aspect of the invention are analogous to those which have been already outlined with reference to the first aspect and which will not be herein repeated.

Preferably, the step of deflecting electromagnetic radiation comprises at least one of the following: deflecting electromagnetic radiation travelling parallel to the longitudinal axis towards said imaging sensor device by means of an optical deflection system positioned in front of the first end of the elongated object so as to form an image of the first end of the elongated object; deflecting electromagnetic radiation travelling parallel to the longitudinal axis towards said imaging sensor device by means of the optical deflection system positioned in front of the second end of the elongated object axially opposite to the first end so as to form an image of the second end of the elongated object. An image of the first or the second end of the elongated object, or of both, can be obtained using the same optical deflection system. A single optical deflection system, for example a single mirror or a single prism, can be used to obtain an image of both ends of the elongated objects, minimizing the number of different elements to be used.

Preferably, between the step of deflecting electromagnetic radiation travelling parallel to the longitudinal axis towards said imaging sensor device by means of the optical deflection system positioned in front of the first end of the elongated object so as to form an image of the first end of the elongated object; and the step of deflecting electromagnetic radiation travelling parallel to the longitudinal axis towards said imaging sensor device by means of the optical deflection system positioned in front of the second end of the elongated object axially opposite to the first end so as to form an image of the second end of the elongated object; the method includes the step of rotating the optical deflection system. No rotation of the elongated object may be needed in order to obtain an image of its opposite axial ends.

Preferably, between the step of deflecting electromagnetic radiation travelling parallel to the longitudinal axis towards said imaging sensor device by means of the optical deflection system positioned in front of the first end of the elongated object so as to form an image of the first end of the elongated object; and the step of deflecting electromagnetic radiation travelling parallel to the longitudinal axis towards said imaging sensor device by means of the optical deflection system positioned in front of the second end of the elongated object axially opposite to the first end so as to form an image of the second end of the elongated object; the method includes the step of moving the elongated object along the transport direction. The rotation of the optical deflection system is realized preferably together with the translation of the elongated object so that the second end can be reflected in the optical deflection system towards the imaging sensor device.

Preferably, the method comprises obtaining an image of a side surface of the elongated object, said side surface being substantially parallel to the longitudinal axis of the elongated object. More preferably, the method comprises obtaining an image of a first side surface of the elongated object;

rotating the elongated object along the longitudinal axis; and obtaining an image of a second side surface of the elongated object rotated with respect to the first side surface. An image of more than one side of the elongated object can be obtained. The images of different sides may be in the number of two, for a rotation along the longitudinal axis preferably of about 180°, or more than two, for a rotation along the longitudinal axis of an angle preferably smaller than 180°. Images of a lateral surface of the elongated object can therefore be obtained.

Preferably, the method according to the invention comprises determining a dimension of said elongated object from the image.

Preferably, the method of the second aspect is performed using the apparatus of the first aspect.

The invention may relate to an apparatus for acquiring data relative to a dimension of an elongated object defining a longitudinal axis and a first and a second end, the apparatus comprising: an imaging sensor device defining a field of view and an optical axis, the imaging sensor device being adapted to image the elongated object in the field of view; a transporting device adapted to position the elongated object in the field of view and to transport the elongated object in a transport direction substantially parallel to the longitudinal axis of the elongated object and forming an angle with the optical axis; an illuminating device adapted to emit electromagnetic radiation to illuminate the elongated object in the field of view; and an optical deflection system including an optical deflector which is adapted to be movable between a first operative position where it is located outside the field of view of the imaging sensor device and a second operative position where it is located within the field of view of the imaging sensor device, and which is adapted to deflect electromagnetic radiation travelling parallel to the longitudinal axis towards said imaging sensor device so as to obtain an image of the first or of the second end of the elongated object.

Further advantages of the invention will become apparent from the detailed description thereof with no-limiting reference to the appended drawings:

FIGS. 1-3 are schematic perspective views of an apparatus for acquiring data relative to a dimension of an elongated object according to the present invention, in three different operative configurations.

With reference to the figures, an apparatus for acquiring data relative to a dimension of an elongated object according to the present invention is globally indicated with reference number 100.

The elongated object 10 defines a longitudinal axis 12 and a first and a second end 14, 16.

The apparatus 100 comprises an imaging sensor device 20, a transporting device 30, an illuminating device 40 and an optical deflection system 50.

The imaging sensor device 20 defines a field of view 22 and an optical axis 24. The elongated object 10 is located in the field of view 22, so that the imaging sensor device 20 images the elongated object 10. Further, the imaging sensor device 20 may define a focus plane, that is a plane the object lying in which are focussed in the imaging sensor device.

The transporting device 30 is associated to the elongated object 10 (for the sake of simplicity in the figures, the transporting device 30 is shown only in FIGS. 1, 2). The transporting device 30 positions the elongated object 10 in the field of view 22 and transports the elongated object 10 in a transport direction 32 substantially parallel to the longitudinal axis 12 of the elongated object 10. The transport direction 32 forms an angle with the optical axis 24.

Preferably, the transport direction 32 is substantially perpendicular to the optical axis 32 (see FIGS. 1-3), the transport direction 32 being depicted as an arrow in FIG. 2.

Preferably, the transporting device 30 can also rotate the elongated object 10 around the longitudinal axis 12.

The image sensor device 20 includes an image sensor 26 and an image sensor holder 28 (for the sake of simplicity in the figures, the image sensor holder 28 is shown only in FIG. 1). The image sensor holder 28 translates the image sensor 26 along the optical axis 24.

The image sensor 26 can be a fixed focus camera and preferably the transporting device 30 transports the elongated object 10 along the transport direction 32 lying in a fixed focus plane of the imaging sensor device 20.

The illuminating device 40 emits electromagnetic radiation to illuminate the elongated object 10 in the field of view 22, as shown in FIG. 1 (for the sake of simplicity in the figures, the illuminating device 40 is shown only in FIG. 1).

As shown in the non-limiting example of FIG. 1, the illuminating device 40 comprises a back light 42 positioned along the optical axis 24 on an opposite side as the imaging sensor device 20 with respect to the transport direction. The back light 42 irradiates a surface 18 of the elongated object 10 facing the back light 42.

Alternatively or in addition, the illuminating device 40 comprises a front light (not shown in the figures) positioned along the optical axis 24 on a same side as imaging sensor device 20 with respect to the transport direction. The front light irradiates a surface of the elongated object 10 facing the imaging sensor device 20.

The optical deflection system 50 includes an optical deflector 52 and an optical deflector holder 54.

The optical deflector 52 is movable between a first operative position where it is located outside the field of view 22 of the imaging sensor device 20 (see FIG. 1) and a second operative position where it is located within the field of view 22 of the imaging sensor device 20 (see FIGS. 2, 3). The optical deflector 52 deflects electromagnetic radiation travelling parallel to the longitudinal axis 12 towards the imaging sensor device 20 so as to obtain an image of the first or of the second end 14, 16 of the elongated object 10 (see FIGS. 2 and 3, respectively).

In the non-limiting example of FIGS. 2 and 3, the optical detector 52 includes a prism which is positioned in front of the two ends 14, 16 of the elongated object 10, respectively. The prism has a facet 53 angled with respect to the transport direction 32.

Preferably, an angle formed between the transport direction 32 and the facet 53 of the prism is comprised between about 30° and about 60°, and more preferably such an angle is of about 45° (see FIGS. 2, 3).

In the second operative position, the optical deflector 52 is located at a geometrical intersection between the transport direction 32 and the optical axis 24 (see FIG. 2). The optical deflector 52 is positioned along the longitudinal axis 12 of the elongated object 10.

The optical deflector holder 54 rotates the optical deflector 52 so that the second operative position comprises a first sub-position and a second sub-position, shown in FIGS. 2 and 3, respectively. In the first sub-position, electromagnetic radiation travels parallel to the longitudinal axis 12 in a first versus and is deflected towards the imaging sensor device 20 so as to obtain an image of the first end 14 of the elongated object 10. In the second sub-position, electromagnetic radiation travels parallel to the longitudinal axis 12 in a second versus (substantially opposite to the first versus) and is deflected towards the imaging sensor device 20 so as to obtain an image of the second end 16 of the elongated object 10.

The apparatus 100 further comprises an elaborating unit (not shown in the figures) which computes a value of a dimension of the elongated object 10 from the image acquired by the imaging sensor device 20.

The operation of the apparatus 100 is already clear from the above, and it is pointed out below.

The elongated object 10 is moved along the transport direction 32 parallel to the longitudinal axis 12 and forming an angle preferably of about 90° with the optical axis 24 in the field of view 22 of the imaging sensor device 20. The elongated object 10 is then positioned in a position within the field of view of the imaging sensor device 20.

The position of the imaging sensor device 20 with respect to the elongated object is then preferably adjusted, for example translating the imagining sensor device 20 along the optical axis of the same, so that the transport direction lies in a focus plane of the imagining sensor device 20. However the following method may be performed using a different apparatus.

The elongated object 10 is irradiated by means of electromagnetic radiation. Preferably it is irradiated with electromagnetic radiation directed substantially perpendicular to the transport direction.

Preferably, when the elongated object is within the field of view of the imagining sensor device 20, an image of a side of the elongated object 10 located on the same side as the imaging sensor device 20 with respect to the transport direction is obtained by means of the imaging sensor device 20. Preferably, the elongated object 10 is then rotated along the longitudinal axis 12 of about 180° and an image of an opposite side of the elongated object, now also facing the imaging sensor device, is taken.

Preferably, before the elongated object 10 is positioned in front to the imaging sensor device 20, the optical deflector 52 of the optical deflector system is positioned from a first operative position away from the field of view of the imaging sensor device 20 depicted in FIG. 1 to a second operative position where it is at an intersection between the optical axis and the transport direction, as depicted in FIG. 2. The electromagnetic radiation travelling parallel to the longitudinal axis 12 is deflected towards the imaging sensor device 20, so that an image of one of the ends 14, 16 of the elongated object 10, preferably first end 14, can be formed by the imaging sensor device 20.

In particular, the electromagnetic radiation travelling parallel to the longitudinal axis 12 is deflected by means of the optical deflection system 50 when it is positioned in front of the first end 14 of the elongated object 10 so as to form an image of the first end 14 of the elongated object 10. In this first configuration, the optical deflector holder 54 rotates the optical deflector 52 in the above-mentioned first sub-position of the second operative position (see FIG. 2).

Preferably, after an image of an end of the elongated object 10 has been taken, the optical deflection system 50 returns in the first operative position. The elongated object 10 is then moved along the transport direction. When the elongated object has been moved within the field of view of the imaging sensor device 20 and for example an image of one or two sides of the elongated object has been taken, the optical deflection system is moved back to the second operative position, as depicted in FIG. 3.

The electromagnetic radiation travelling parallel to the longitudinal axis 12 is deflected by means of the optical deflection system 50 when it is positioned in front of the second end 16 of the elongated object 10 axially opposite to the first end 14, so that an image of the second end 16 of the elongated object 10 may be formed by the imaging sensor device 20. In this second configuration, the optical deflector holder 54 rotates the optical deflector 52 in the above-mentioned second sub-position of the second operative position (see FIG. 3).

Therefore, between the above-mentioned first and second sub-positions, the optical deflector 52 of the optical deflection system 50 is rotated, that is the second position includes two sub-positions which differ in the angular position of the optical deflector 52.

Furthermore, between the above-mentioned first and second sub-positions, the elongated object 10 is moved along the transport direction 32.

Preferably, the operation of the apparatus 100 comprises obtaining an image of a side surface of the elongated object 10. This side surface is substantially parallel to the longitudinal axis 12 of the elongated object 10.

More preferably, an image of a first side surface of the elongated object 10 is obtained, then the elongated object 10 is rotated along the longitudinal axis 12, and an image of a second side surface of the elongated object 10 is obtained, which is rotated with respect to the first side surface.

The invention claimed is:

1. An apparatus for acquiring data relative to a dimension of an elongated object defining a longitudinal axis and a first and a second end, the apparatus comprising:
  an imaging sensor device defining a field of view and an optical axis, the imaging sensor device being adapted to image the elongated object in the field of view;
  a transporting device adapted to position the elongated object in the field of view and to transport the elongated object in a transport direction substantially parallel to the longitudinal axis of the elongated object and forming an angle with the optical axis;
  an illuminating device adapted to emit electromagnetic radiation to illuminate the elongated object in the field of view; and
  an optical deflection system including an optical deflector which is adapted to be movable between a first operative position and a second operative position and which is adapted, in the second operative position, to deflect electromagnetic radiation travelling parallel to the longitudinal axis towards said imaging sensor device so as to obtain an image of the first or of the second end of the elongated object;
  wherein the optical deflection system includes an optical deflector holder adapted to rotate the optical deflector so that the second operative position comprises a first sub-position in which electromagnetic radiation travelling parallel to the longitudinal axis in a first versus is deflected towards said imaging sensor device so as to obtain an image of the first end of the elongated object and a second sub-position in which electromagnetic radiation travelling parallel to the longitudinal axis in a second versus is deflected towards said imaging sensor device so as to obtain an image of the second end of the elongated object.

2. The apparatus according to claim 1, wherein said optical detector includes a prism adapted to be positioned in front of an end of the elongated object and having a facet angled with respect to the transport direction.

3. The apparatus according to claim 2, wherein an angle formed between the transport direction and the facet of the prism is comprised between about 30° and about 60°.

4. The apparatus according to claim 3, wherein the angle formed between the transport direction and the facet of the prism is of about 45°.

5. The apparatus according to claim 1, wherein the transport direction is substantially perpendicular to the optical axis.

6. The apparatus according to claim 5, wherein the imaging sensor device includes a fixed focus camera and said transporting device is adapted to transport said elongated object along the transport direction lying in a fixed focus plane of said imaging sensor device.

7. The apparatus according to claim 1, wherein the transporting device is adapted to rotate the elongated object around the longitudinal axis.

8. The apparatus according to claim 1, wherein in said second operative position the optical deflector is located at a geometrical intersection between the transport direction and the optical axis.

9. The apparatus according to claim 1, wherein the image sensor device includes an image sensor holder and an image sensor, the image sensor holder being adapted to translate the image sensor along the optical axis.

10. The apparatus according to claim 1, wherein the illuminating device comprises one or more of the following:
a back light positioned along the optical axis on an opposite side of the transport direction with respect to the imaging sensor device, the back light being adapted to irradiate a surface of the elongated object facing the back light;
a front light positioned along the optical axis on a same side of the transport direction with respect to the imaging sensor device, the front light being adapted to irradiate a surface of the elongated object facing the imaging sensor device.

11. The apparatus according to claim 1, comprising:
an elaborating unit, adapted to compute a value of a dimension of the elongated object from the image acquired by the imaging sensor device.

12. A method for acquiring data relative to a dimension of an elongated object defining a longitudinal axis and having a first and a second end, the method comprising the step of:
providing an imaging sensor device having an optical axis and a field of view;
moving the elongated object along a transport direction parallel to the longitudinal axis and forming an angle with the optical axis in the field of view of the imaging sensor device;
irradiating the elongated object by means of electromagnetic radiation; and
deflecting electromagnetic radiation travelling parallel to the longitudinal axis towards said imaging sensor device so as to form an image of one of the ends of the elongated object;
wherein the step of deflecting electromagnetic radiation comprises at least one of the following:
deflecting electromagnetic radiation travelling parallel to the longitudinal axis towards said imaging sensor device by means of an optical deflection system positioned in front of the first end of the elongated object so as to form an image of the first end of the elongated object;
deflecting electromagnetic radiation travelling parallel to the longitudinal axis towards said imaging sensor device by means of the optical deflection system positioned in front of the second end of the elongated object axially opposite to the first end so as to form an image of the second end of the elongated object.

13. The method according to claim 12, wherein between the step of:
deflecting electromagnetic radiation travelling parallel to the longitudinal axis towards said imaging sensor device by means of the optical deflection system positioned in front of the first end of the elongated object so as to form an image of the first end of the elongated object; and the step of:
deflecting electromagnetic radiation travelling parallel to the longitudinal axis towards said imaging sensor device by means of the optical deflection system positioned in front of the second end of the elongated object axially opposite to the first end so as to form an image of the second end of the elongated object; the method includes the step of:
rotating the optical deflection system.

14. The method according to claim 12, wherein between the step of:
deflecting electromagnetic radiation travelling parallel to the longitudinal axis towards said imaging sensor device by means of the optical deflection system positioned in front of the first end of the elongated object so as to form an image of the first end of the elongated object; and the step of:
deflecting electromagnetic radiation travelling parallel to the longitudinal axis towards said imaging sensor device by means of the optical deflection system positioned in front of the second end of the elongated object axially opposite to the first end so as to form an image of the second end of the elongated object; the method includes the step of:
moving the elongated object along the transport direction.

15. The method according to claim 12, comprising:
obtaining an image of a side surface of the elongated object, said side surface being substantially parallel to the longitudinal axis of the elongated object.

16. The method according to claim 12, including:
obtaining an image of a first side surface of the elongated object;
rotating the elongated object along the longitudinal axis; and
obtaining an image of a second side surface of the elongated object rotated with respect to the first side surface.

17. The method according to claim 12, comprising:
determining a dimension of said elongated object from the image.

18. The method according to claim 12 using the apparatus for acquiring data relative to a dimension of an elongated object defining a longitudinal axis and a first and a second end, the apparatus comprising:
an imaging sensor device defining a field of view and an optical axis, the imaging sensor device being adapted to image the elongated object in the field of view;
a transporting device adapted to position the elongated object in the field of view and to transport the elongated object in a transport direction substantially parallel to the longitudinal axis of the elongated object and forming an angle with the optical axis;
an illuminating device adapted to emit electromagnetic radiation to illuminate the elongated object in the field of view; and
an optical deflection system including an optical deflector which is adapted to be movable between a first operative position and a second operative position and which is adapted, in the second operative position, to deflect electromagnetic radiation travelling parallel to the longitudinal axis towards said imaging sensor device so as to obtain an image of the first or of the second end of the elongated object;

wherein the optical deflection system includes an optical deflector holder adapted to rotate the optical deflector so that the second operative position comprises a first sub-position in which electromagnetic radiation travelling parallel to the longitudinal axis in a first versus is deflected towards said imaging sensor device so as to obtain an image of the first end of the elongated object and a second sub-position in which electromagnetic radiation travelling parallel to the longitudinal axis in a second versus is deflected towards said imaging sensor device so as to obtain an image of the second end of the elongated object.

* * * * *